(12) United States Patent
Wang et al.

(10) Patent No.: US 9,427,155 B2
(45) Date of Patent: Aug. 30, 2016

(54) OPTICAL APPARATUS AND OPERATING METHOD THEREOF

(71) Applicant: Crystalvue medical corporation, Taoyuan (TW)

(72) Inventors: William Wang, Taoyuan (TW); Chung-Ping Chuang, Taoyuan (TW); Meng-Shin Yen, Taipei (TW); Chung-Cheng Chou, Luzhu Township (TW)

(73) Assignee: Crystalvue medical corporation, Taoyuan (TW)

( * ) Notice: Subject to any disclaimer, the term of this patent is extended or adjusted under 35 U.S.C. 154(b) by 462 days.

(21) Appl. No.: 14/060,435

(22) Filed: Oct. 22, 2013

(65) Prior Publication Data

US 2014/0114145 A1 Apr. 24, 2014

Related U.S. Application Data

(60) Provisional application No. 61/718,176, filed on Oct. 24, 2012.

(51) Int. Cl.
*A61B 3/16* (2006.01)
*A61B 3/18* (2006.01)
*A61B 3/107* (2006.01)

(52) U.S. Cl.
CPC .............. *A61B 3/18* (2013.01); *A61B 3/107* (2013.01); *A61B 3/16* (2013.01); *A61B 3/165* (2013.01)

(58) Field of Classification Search
CPC ........ A61B 3/16; A61B 3/107; A61B 3/165; A61B 3/18
See application file for complete search history.

(56) References Cited

U.S. PATENT DOCUMENTS

2013/0165763 A1* 6/2013 Huang .................... A61B 3/16
600/401

\* cited by examiner

*Primary Examiner* — Joseph Dietrich
(74) *Attorney, Agent, or Firm* — Patterson + Sheridan, LLP

(57) ABSTRACT

The optical apparatus includes an optical measurement module, a central processing module, and an air-puff module. The air-puff module is used for generating an air pressure to a surface of the cornea according a blow pattern to cause a deformation of the cornea. The optical measurement module includes a first unit and a second unit. The first unit is used for measuring an intraocular pressure (IOP) of the eye according to the deformation of the cornea. The second unit is used for measuring properties of the cornea in an optical interference way. The central processing module is coupled to the first unit and the second unit and used for receiving and processing the intraocular pressure and the properties of the cornea to provide a result.

8 Claims, 4 Drawing Sheets

OPTICAL APPARATUS AND OPERATING METHOD THEREOF

CROSS-REFERENCE TO RELATED APPLICATIONS

This non-provisional application claims benefit of U.S. Provisional Application Ser. No. 61/718,176, filed on Oct. 24, 2012, which is incorporated by reference in its entirety.

BACKGROUND OF THE INVENTION

1. Field of the Invention

This invention relates to optical apparatus, especially to an optical apparatus and an optical apparatus operating method used for providing information of intraocular pressure (IOP), cornea properties (e.g., elasticity, viscosity), and eye weight.

2. Description of the Prior Art

Due to its characteristics of non-invasion and fast response, the optical apparatus is widely used for non-contact measurement or inspection, especially in medical applications. For example, a published application (TW 101106376) shows a technology using optical interference to measure material properties of the sample.

Please refer to FIG. 1. FIG. 1 illustrates a schematic diagram of a conventional non-contact tonometer disclosed in a prior art. As shown in FIG. 1, the non-contact tonometer 1 at least includes an air-puff unit AP, an optical emitting unit EU, and an optical receiving unit RU. The air-puff unit AP is used to generate an air pressure G to a sample SA (e.g., an eyeball). The optical emitting unit EU is used to emit an incident light L1 to the sample SA. The optical receiving unit RU is used to receive the reflected light L2 reflected by the sample SA. When the air pressure G reaches a surface of the cornea CA of the eyeball, the deformation of the cornea CA caused by the air pressure G will be detected by the optical receiving unit RU. The relationship between the applied force (evaluated from the air pressure G) and the deformation of the corneal CA will provide sufficient information for calculating an intraocular pressure of the eyeball. However, the conventional non-contact tonometer 1 fails to acquire other reference data about the cornea CA, such as the elasticity, viscosity, and central corneal thickness (CCT) of the cornea CA . . . etc, at the same time.

Therefore, the invention provides an optical apparatus and an optical apparatus operating method to solve the above-mentioned problems occurred in the prior arts.

SUMMARY OF THE INVENTION

An embodiment of the invention is an optical apparatus used for non-contact inspection and measurement of a cornea of an eye. In this embodiment, the optical apparatus includes an optical measurement module, a central processing module, and an air-puff module. The air-puff module is used for generating an air pressure to a surface of the cornea according a blow pattern to cause a deformation of the cornea. The optical measurement module includes a first unit and a second unit. The first unit is used for measuring an intraocular pressure (IOP) of the eye according to the deformation of the cornea. The second unit is used for measuring properties of the cornea in an optical interference way. The central processing module is coupled to the first unit and the second unit and used for receiving and processing the intraocular pressure and the properties of the cornea to provide a result.

In an embodiment, the properties of the cornea include an elasticity of the cornea, a viscosity of the cornea, a central corneal thickness (CCT) of the cornea, a profile of the cornea, and a curvature of the cornea.

In an embodiment, the optical apparatus further includes a target confirming module used for confirming that the cornea of the eye is the target of the optical apparatus at first.

In an embodiment, the second unit includes an optical source, a coupling unit, and a reference reflector, the optical source emits an incident light to the coupling unit, and the coupling unit divides the incident light into a reference incident light emitted to the reference reflector and a sample incident light emitted to the cornea of the eye respectively; when the cornea is not deformed by the air pressure generated by the air-puff module, the coupling unit receives a reference reflected light reflected by the reference reflector and a first sample reflected light reflected by the un-deformed cornea respectively and generates a first optical interference result, the central processing module generates a corneal tomography image of the cornea according to the first optical interference result and obtains a central corneal thickness (CCT) of the cornea, a profile of the cornea, and a curvature of the cornea according to the corneal tomography image of the cornea; after the cornea is deformed by the air pressure generated by the air-puff module, the coupling unit receives the reference reflected light reflected by the reference reflector and a second sample reflected light reflected by the deformed cornea respectively and generates a second optical interference result, and the central processing module compares the first optical interference result with the second optical interference result to evaluate an elasticity of the cornea, a viscosity of the cornea, and a weight of the eye.

In an embodiment, the blow pattern includes duration of the air pressure, a magnitude of the air pressure, and a frequency of the air pressure.

In an embodiment, the first unit includes an optical emitter and an optical receiver; before the cornea is deformed, the optical emitter emits a first sensing light to the surface of the un-deformed cornea and the optical receiver receives a first reflected light reflected by the un-deformed cornea; after the cornea is deformed, the optical emitter emits a second sensing light to the surface of the deformed cornea and the optical receiver receives a second reflected light reflected by the deformed cornea, the central processing module obtains a signal variation between the first reflected light and the second reflected light and links the signal variation with the blow pattern to evaluate the intraocular pressure (IOP) of the eye.

Another embodiment of the invention is a method of operating an optical apparatus for non-contact inspection and measurement of a cornea of an eye. In this embodiment, the optical apparatus includes an air-puff module, an optical measurement module, and a central processing module. The optical measurement module includes a first unit and a second unit. The method includes steps of: (a) the second unit measuring properties of the cornea in an optical interference way; (b) the air-puff module generating an air pressure to a surface of the cornea according a blow pattern to cause a deformation of the cornea; (c) the first unit measuring an intraocular pressure (IOP) of the eye according to the deformation of the cornea; and (d) the central processing module receiving and processing the intraocular pressure and the properties of the cornea to provide a result.

Compared to the prior art, the optical apparatus and the optical apparatus operating method of the invention can provide more functions than a conventional non-contact tonometer to provide information of the intraocular pressure (IOP), the cornea properties (elasticity, viscosity, CCT), and eye weight at the same time.

The advantage and spirit of the invention may be understood by the following detailed descriptions together with the appended drawings.

BRIEF DESCRIPTION OF THE APPENDED DRAWINGS

DETAILED DESCRIPTION OF THE INVENTION

Figure 1:
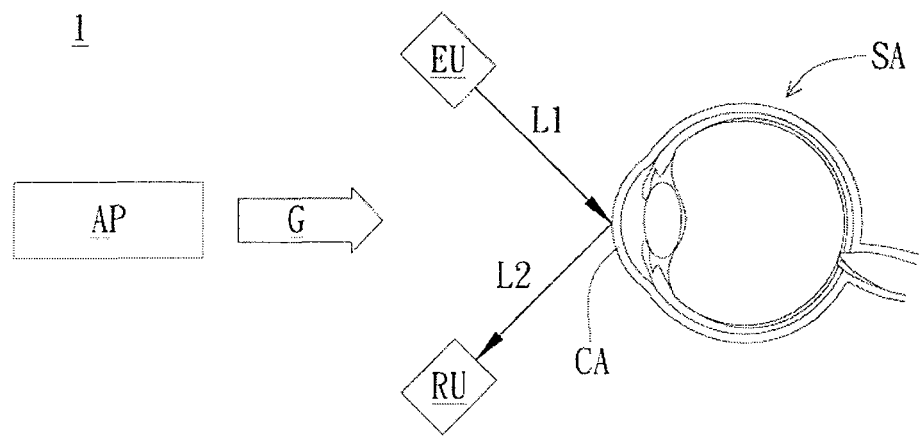
FIG. 1 illustrates a schematic diagram of a conventional non-contact tonometer disclosed in a prior art.
Figure 2:
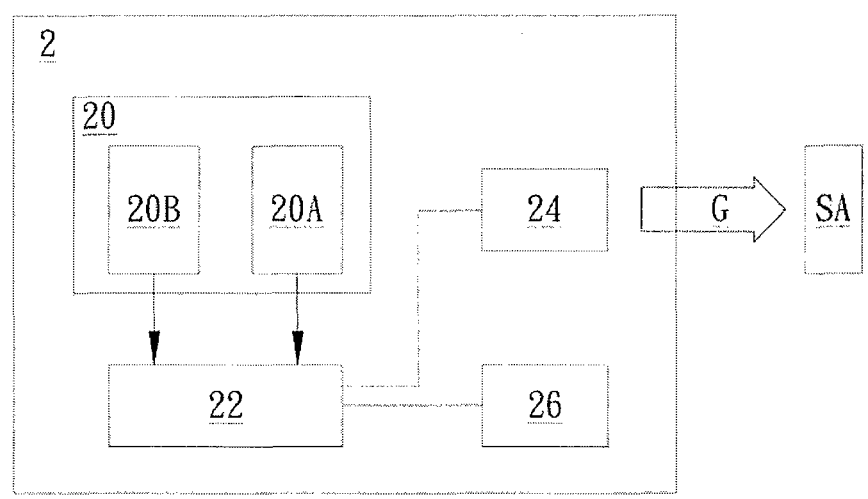
FIG. 2 illustrates a function block diagram of the optical apparatus in an embodiment.

An embodiment of the invention is an optical apparatus used for non-contact inspection and measurement of a cornea of an eye. Please refer to FIG. 2. FIG. 2 illustrates a function block diagram of the optical apparatus in this embodiment.

As shown in FIG. 2, the optical apparatus 2 includes an optical measurement module 20, a central processing module 22, an air-puff module 24, and a target confirming module 26. The optical measurement module 20 includes a first unit 20A and a second unit 20B. The central processing module 22 is coupled to the first unit 20A and the second unit 20B. It should be noticed that if ignoring the massive calculation and cost, the first unit 20A can be replaced by the second unit 20B.

In this embodiment, the target confirming module 26 is used for confirming that the sample SA (e.g., the cornea of the eye) is the target of the optical apparatus 2 at first. Then, the air-puff module 24 is used for generating an air pressure G to the sample SA according to a blow pattern to cause a deformation of the sample SA. In fact, the blow pattern can include duration of the air pressure G, a magnitude of the air pressure G, and a frequency of the air pressure G, but not limited to this. For example, if the air-puff module 24 generates the air pressure G according to the blow pattern to a surface of a cornea of an eyeball, it will cause a deformation of the cornea.

The first unit 20A is used for measuring an intraocular pressure (IOP) of the eye according to the deformation of the cornea. The second unit 20B is used for measuring properties of the cornea in an optical interference way.

It should be noticed that the optical apparatus 2 has great flexibility in use. For example, the air-puff module 24 can be not only cooperated with the first unit 20A and the second unit 20B for measurement, but also cooperated with the first unit 20A or the second unit 20B alone for measurement depended on practical needs without any limitations. Besides, the optical measurement module 20 can only use the second unit 20B alone for measuring cornea properties, but not limited to this.

In fact, the properties of the cornea include an elasticity of the cornea, a viscosity of the cornea, a central corneal thickness (CCT) of the cornea, a profile of the cornea, and a curvature of the cornea. The central processing module 22 is used for receiving and processing the intraocular pressure from the first unit 20A and the properties of the cornea from the second unit 20B respectively to provide a result.

Figure 3:
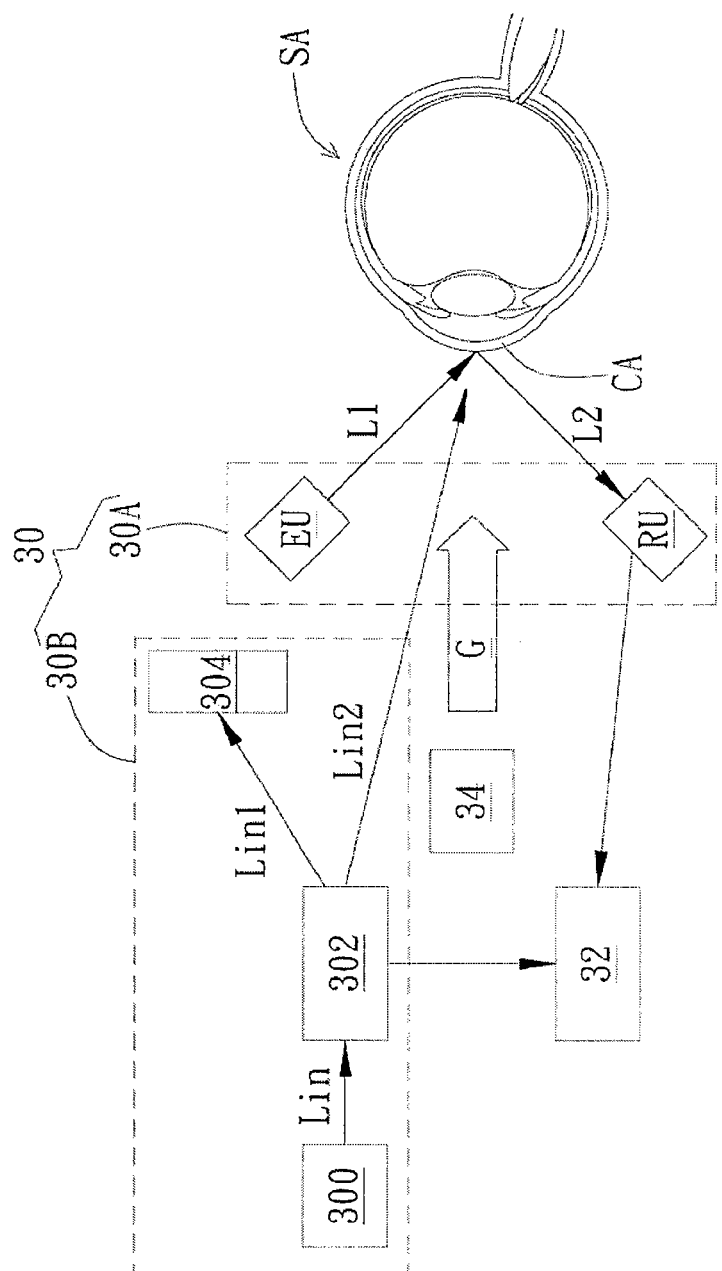
FIG. 3 illustrates a schematic diagram of the optical apparatus in another embodiment.

Please refer to FIG. 3. FIG. 3 illustrates a schematic diagram of the optical apparatus in another embodiment. As shown in FIG. 3, the optical apparatus 3 includes an optical measurement module, a central processing module 32, and an air-puff module 34. The optical measurement module includes a first unit 30A and a second unit 30B.

In this embodiment, the first unit 30A includes an optical emitter EU and an optical receiver RU. Before the cornea CA is deformed by the air pressure G generated from the air-puff module 34 according to a blow pattern, the optical emitter EU emits a first sensing light to the surface of the un-deformed cornea CA and the optical receiver RU receives a first reflected light reflected by the un-deformed cornea CA. After the cornea CA is deformed, the optical emitter EU emits a second sensing light to the surface of the deformed cornea CA and the optical receiver RU receives a second reflected light reflected by the deformed cornea CA. The central processing module 32 is coupled to the optical receiver RU and obtains a signal variation between the first reflected light and the second reflected light and links the signal variation with the used blow pattern to evaluate the intraocular pressure (IOP) of the eye.

The second unit 30B includes an optical source 300, a coupling unit 302, and a reference reflector 304. The optical source 300 emits an incident light Lin to the coupling unit 302, and the coupling unit 302 will divide the incident light Lin into a reference incident light Lin1 emitted to the reference reflector 304 and a sample incident light Lin2 emitted to the surface of the cornea CA respectively. After the reference incident light Lin1 and the sample incident light Lin2 are emitted to the reference reflector 304 and the surface of the cornea CA respectively, the reference reflector 304 and the surface of the cornea CA will reflect the reference incident light Lin1 and the sample incident light Lin2 respectively.

When the cornea CA is not deformed by the air pressure G generated from the air-puff module 34 according to the blow pattern, the coupling unit 302 will receive a reference reflected light reflected by the reference reflector 304 and a first sample reflected light reflected by the surface of the un-deformed cornea CA respectively and generate a first optical interference result. Afterward, the central processing module 32 will generate a corneal tomography image of the un-deformed cornea CA according to the first optical interference result and obtain a central corneal thickness (CCT) of the cornea CA, a profile of the cornea CA, and a curvature of the cornea CA according to the corneal tomography image of the un-deformed cornea CA.

After the cornea CA is deformed by the air pressure G generated from the air-puff module 34 according to the blow pattern, the coupling unit 302 will receive the reference reflected light reflected by the reference reflector 304 and a second sample reflected light reflected by the deformed cornea CA respectively and generate a second optical interference result. Then, the central processing module 32 will compare the first optical interference result with the second optical interference result to evaluate an elasticity and a viscosity of the cornea CA, and a weight of the eye.

In fact, if the reference reflector 304 is fixed, the reference reflected light reflected by the reference reflector 304 will be also unchanged. Since the coupling unit 302 will receive the first sample reflected light reflected by the surface of the un-deformed cornea CA and the second sample reflected light reflected by the deformed cornea CA, the central processing module 32 can also compare the first sample reflected light and the second sample reflected light to evaluate the deformation of the cornea CA, but not limited to this.

In this embodiment, the properties of the cornea CA such as elasticity, viscosity or weight are derived from force-motion relationship. Please refer to the equations shown below for motion-force relationship.

$$F=kx \qquad \text{(Equation 1)}$$

In Equation 1, k represents a spring constant, and once force and displacement are confirmed, then k can be evaluated. More properties can be added for Equation 2 for more complex system (more closing real system) such as:

$$F=kx+cx'+mx'' \qquad \text{(Equation 2)}$$

Wherein c represents a damping factor and m represents mass respectively. And Equation 2 can be explored to a matrix for cornea properties measurement by different applied force at different points, as shown in Equations 3a~3c:

$$F_1=kx_1+cx_1'+mx_1'' \qquad \text{(Equation 3a)}$$

$$F_2=kx_2+cx_2'+mx_2'' \qquad \text{(Equation 3b)}$$

$$F_3=kx_3+cx_3'+mx_3'' \qquad \text{(Equation 3c)}$$

Equation 3a~3c can be also shown in a matrix form:

$$\begin{pmatrix} F_1 \\ F_2 \\ F_3 \end{pmatrix} = \begin{pmatrix} x_1 & x_1' & x_1'' \\ x_2 & x_2' & x_2'' \\ x_3 & x_3' & x_3'' \end{pmatrix} \begin{pmatrix} k \\ c \\ m \end{pmatrix}$$

Figure 4A:
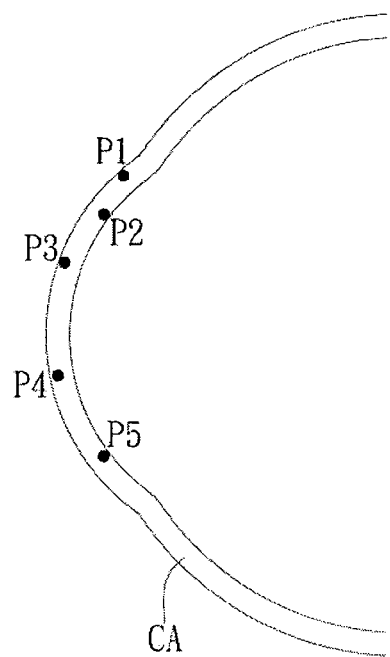
FIG. 4A illustrates a cross-sectional diagram of the cornea having measured points at different positions.
Figure 4B:
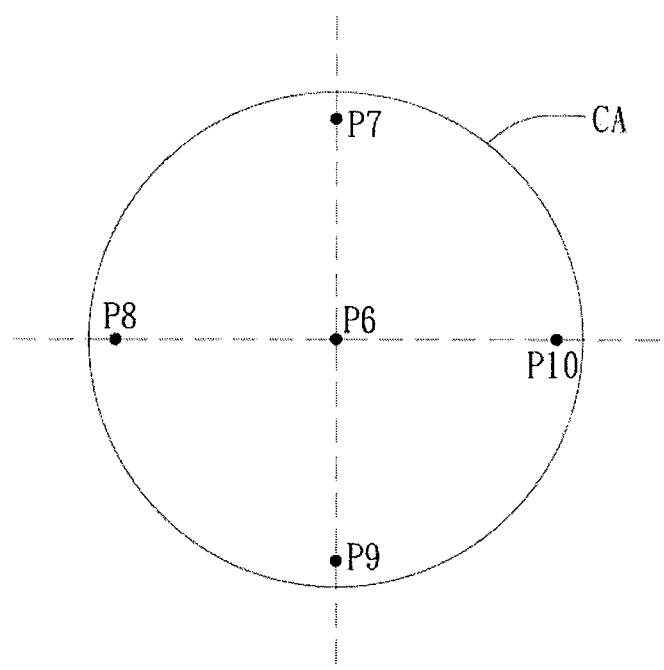
FIG. 4B illustrates a front-view of the cornea having measured points at different positions.

Since the cornea tomography is established by optical interference, in practical applications, the measured points of cornea CA can be widely chosen at different positions of the cornea CA, no matter at the surface of the cornea CA or inside the cornea CA, as the measured points P1~P5 shown in FIG. 4A and the measured points P6~P10 shown in FIG. 4B.

The displacement x, velocity x', and acceleration x" all can be acquired from a predict distance which reference end set by different locations (concept just same as recording time duration while deformed one point to another point). Of course the frequency domain optical coherence tomography skill can be implemented here if fast speed is first priority.

Another embodiment of the invention is a method of operating an optical apparatus for non-contact inspection and measurement of a cornea of an eye. In this embodiment, the optical apparatus includes an air-puff module, an optical measurement module, a central processing module, and a target confirming module. The optical measurement module includes a first unit and a second unit. It should be noticed that the optical apparatus has great flexibility in use. For example, the air-puff module can be not only cooperated with the first unit and the second unit for measurement, but also cooperated with the first unit or the second unit alone for measurement depended on practical needs without any limitations. Besides, the optical measurement module can only use the second unit alone for measuring cornea properties, but not limited to this.

Figure 5:
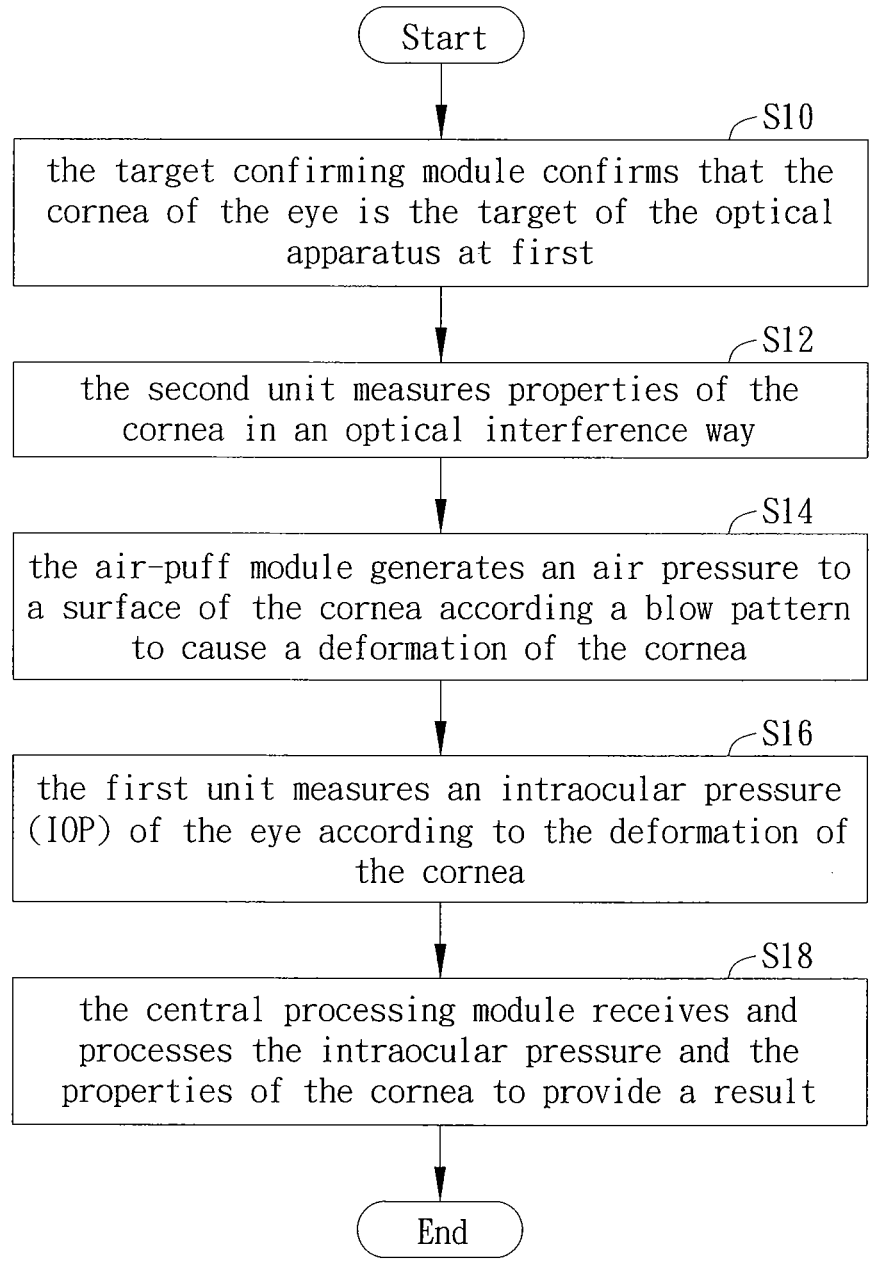
FIG. 5 illustrates a flow chart of the optical apparatus operating method in another embodiment.

Please refer to FIG. 5. FIG. 5 illustrates a flow chart of the optical apparatus operating method in this embodiment. As shown in FIG. 5, in the step S10, the target confirming module confirms that the cornea of the eye is the target of the optical apparatus at first. In the step S12, the second unit measures properties of the cornea in an optical interference way. In the step S14, the air-puff module generates an air pressure to a surface of the cornea according a blow pattern to cause a deformation of the cornea. In the step S16, the first unit measures an intraocular pressure (IOP) of the eye according to the deformation of the cornea. In the step S18, the central processing module receives and processes the intraocular pressure and the properties of the cornea to provide a result.

Compared to the prior art, the optical apparatus and the optical apparatus operating method of the invention can provide more functions than a conventional non-contact tonometer to provide information of the intraocular pressure (IOP), the cornea properties (elasticity, viscosity, CCT), and eye weight at the same time.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An optical apparatus, for non-contact inspection and measurement of a cornea of an eye, the optical apparatus comprising:
   an air-puff module, for generating an air pressure to a surface of the cornea according a blow pattern comprising duration of the air pressure, a magnitude of the air pressure and a frequency of the air pressure to cause a deformation of the cornea;
   a central processing module; and
   an optical measurement module, comprising:
      a first unit, for measuring an intraocular pressure (IOP) of the eye according to the deformation of the cornea, wherein the first unit comprises an optical emitter and an optical receiver; before the cornea is deformed, the optical emitter is configured to emit a first sensing light to the surface of the un-deformed cornea and the optical receiver is configured to receive a first reflected light reflected by the un-deformed cornea; after the cornea is deformed, the optical emitter is configured to emit a second sensing light to the surface of the deformed cornea and the optical receiver receives a second reflected light reflected by the deformed cornea, the central processing module is configured to obtain a signal variation between the first reflected light and the second reflected light and link the signal variation with the duration of the air pressure, the magnitude of the air pressure and the frequency of the air pressure of the blow pattern to evaluate the intraocular pressure (IOP) of the eye; and
      a second unit, for measuring properties of the cornea in an optical interference way;
   wherein the central processing module is coupled to the first unit and the second unit, the central processing module for receiving and processing the intraocular pressure and the properties of the cornea to provide a result.

2. The optical apparatus of claim 1, wherein the properties of the cornea comprise an elasticity of the cornea, a viscosity of the cornea, a central corneal thickness (CCT) of the cornea, a profile of the cornea, and a curvature of the cornea.

3. The optical apparatus of claim 1, further comprising:
a target confirming module, for confirming that the cornea of the eye is the target of the optical apparatus at first.

4. The optical apparatus of claim 1, wherein the second unit comprises an optical source, a coupling unit, and a reference reflector, the optical source emits an incident light to the coupling unit, and the coupling unit divides the incident light into a reference incident light emitted to the reference reflector and a sample incident light emitted to the cornea of the eye respectively, when the cornea is not deformed by the air pressure generated by the air-puff module, the coupling unit receives a reference reflected light reflected by the reference reflector and a first sample reflected light reflected by the un-deformed cornea respectively and generates a first optical interference result, the central processing module generates a corneal tomography image of the cornea according to the first optical interference result and obtains a central corneal thickness (CCT) of the cornea, a profile of the cornea, and a curvature of the cornea according to the corneal tomography image of the cornea; after the cornea is deformed by the air pressure generated by the air-puff module, the coupling unit receives the reference reflected light reflected by the reference reflector and a second sample reflected light reflected by the deformed cornea respectively and generates a second optical interference result, and the central processing module compares the first optical interference result with the second optical interference result to evaluate an elasticity of the cornea, a viscosity of the cornea, and a weight of the eye.

5. A method of operating an optical apparatus for non-contact inspection and measurement of a cornea of an eye, the optical apparatus comprising an air-puff module, an optical measurement module, and a central processing module, the optical measurement module comprising a first unit and a second unit, the method comprising steps of:
(a) the second unit measuring properties of the cornea in an optical interference way;
(b) the air-puff module generating an air pressure to a surface of the cornea according a blow pattern comprising duration of the air pressure, a magnitude of the air pressure and a frequency of the air pressure to cause a deformation of the cornea;
(c) the first unit measuring an intraocular pressure (IOP) of the eye according to the deformation of the cornea, wherein the first unit comprises an optical emitter and an optical receiver; before the cornea is deformed, the optical emitter emits a first sensing light to the surface of the un-deformed cornea and the optical receiver receives a first reflected light reflected by the un-deformed cornea; after the cornea is deformed, the optical emitter emits a second sensing light to the surface of the deformed cornea and the optical receiver receives a second reflected light reflected by the deformed cornea, the central processing module obtains a signal variation between the first reflected light and the second reflected light and links the signal variation with the duration of the air pressure, the magnitude of the air pressure and the frequency of the air pressure of the blow pattern to evaluate the intraocular pressure (IOP) of the eye; and
(d) the central processing module receiving and processing the intraocular pressure and the properties of the cornea to provide a result.

6. The method of claim 5, wherein the properties of the cornea comprise an elasticity of the cornea, a viscosity of the cornea, a central corneal thickness (CCT) of the cornea, a profile of the cornea, and a curvature of the cornea.

7. The method of claim 5, wherein before the step (a), the method further comprises a step of:
confirming that the cornea of the eye is the target of the optical apparatus at first.

8. The method of claim 5, wherein the second unit comprises an optical source, a coupling unit, and a reference reflector, the optical source emits an incident light to the coupling unit, and the coupling unit divides the incident light into a reference incident light emitted to the reference reflector and a sample incident light emitted to the cornea of the eye respectively, when the cornea is not deformed by the air pressure generated by the air-puff module, the coupling unit receives a reference reflected light reflected by the reference reflector and a first sample reflected light reflected by the un-deformed cornea respectively and generates a first optical interference result, the central processing module generates a corneal tomography image of the cornea according to the first optical interference result and obtains a central corneal thickness (CCT) of the cornea, a profile of the cornea, and a curvature of the cornea according to the corneal tomography image of the cornea; after the cornea is deformed by the air pressure generated by the air-puff module, the coupling unit receives the reference reflected light reflected by the reference reflector and a second sample reflected light reflected by the deformed cornea respectively and generates a second optical interference result, and the central processing module compares the first optical interference result with the second optical interference result to evaluate an elasticity of the cornea, a viscosity of the cornea, and a weight of the eye.

* * * * *